US007008650B2

(12) United States Patent
Lam

(10) Patent No.: US 7,008,650 B2
(45) Date of Patent: Mar. 7, 2006

(54) COMPOSITIONS FOR THE TREATMENT OF ACQUIRED IMMUNODEFICIENCY DISEASE

(76) Inventor: Paul Y. S. Lam, 888 S. Figueroa St., Suite 1760, Los Angeles, CA (US) 90017

( * ) Notice: Subject to any disclaimer, the term of this patent is extended or adjusted under 35 U.S.C. 154(b) by 618 days.

(21) Appl. No.: 09/985,460

(22) Filed: Nov. 2, 2001

(65) Prior Publication Data

US 2004/0047926 A1 Mar. 11, 2004

Related U.S. Application Data

(60) Provisional application No. 60/310,831, filed on Aug. 9, 2001.

(51) Int. Cl.
 *A61K 35/78* (2006.01)
(52) U.S. Cl. ............... 424/764; 424/757; 424/773; 424/774; 514/885
(58) Field of Classification Search ........... 424/764, 424/773, 774, 757; 514/783, 885
See application file for complete search history.

(56) References Cited

U.S. PATENT DOCUMENTS

| 4,659,558 A | 4/1987 | Urquhart et al. |
| 4,810,499 A | 3/1989 | Nuwayser |
| 5,204,101 A * | 4/1993 | Stubblefield et al. ....... 424/736 |
| 5,438,040 A | 8/1995 | Ekwiribe |
| 5,629,020 A | 5/1997 | Leone-Bay et al. |
| 5,641,511 A | 6/1997 | Kuhrts |
| 5,648,209 A | 7/1997 | Avrameas et al. |
| 5,654,000 A | 8/1997 | Poli et al. |
| 5,665,592 A | 9/1997 | Tompkins et al. |
| 5,681,811 A | 10/1997 | Ekwuribe |
| 5,690,954 A | 11/1997 | Illum |
| 5,691,183 A | 11/1997 | Franzusoff et al. |
| 5,759,566 A | 6/1998 | Poli et al. |
| 5,766,633 A | 6/1998 | Milstein et al. |
| 5,783,212 A | 7/1998 | Fassihi et al. |
| 5,792,451 A | 8/1998 | Sarubbi et al. |
| 5,849,331 A | 12/1998 | Ducheyne et al. |
| 5,879,712 A | 3/1999 | Bomberger et al. |
| 5,935,601 A | 8/1999 | Leone-Bay et al. |
| 6,002,961 A | 12/1999 | Mitragotri et al. |
| 6,017,318 A | 1/2000 | Gauthier et al. |
| 6,017,536 A | 1/2000 | Barney et al. |
| 6,018,678 A | 1/2000 | Mitragotri et al. |
| 6,041,253 A | 3/2000 | Kost et al. |
| 6,072,041 A | 6/2000 | Davis et al. |
| 6,090,389 A * | 7/2000 | Chen |
| 6,228,608 B1 | 5/2001 | Young et al. |
| 6,254,872 B1 | 7/2001 | Yamamoto |

FOREIGN PATENT DOCUMENTS

| EP | 0441278 A1 * | 2/1991 |
| JP | 62048619 A * | 3/1987 |
| JP | 02053730 A * | 2/1990 |
| JP | 09188621 A * | 7/1997 |

OTHER PUBLICATIONS

Ushio Y. et al., Japanese Journal of Pharmacology (1991), 56(2): 167-175. The effects of Saikosaponin-d on yeast phagocytosis and degradation in peritoneal macrophages: Related increase in Fc receptor expression and altered cytoplasmic organization.*
Ushio Y. et al., Planta Medica (1992), 58(2): 171-173. Inactivation of measles and herpes simple virus by *Saikosaponin* d.*
Murillo-Alvarez J. et al., Pharmaceutical Biology (Feb. 2001), 39(6): 445-449. Antimicrobial and cytotoxic activity of some medicinal plants from Baja California Sur (Mexico).*
Ahn, B.Z. et al., "Inhibitory effect of bupleuri radix saponins on adhesion of some solid tumor cells and relation to hemolytic action: screening of 232 herbal drugs for anti-cell adhesion," Planta Med. Apr. 1998;64(3):220-4.
Bogers, W.M. et al., "Developments in preclinical AIDS vaccine efficacy models," AIDS, 2000;14 Suppl 3:S141-51.
Brunner, D., et al., "Infection of Peritoneal Macrophages In Vitro and In Vivo with Feline Immunodeficiency Virus," J. Virol. 63:5483 (1989).
Chaisson, R.E., "HIV Becomes World's Leading Infectious Cause Of Death," Hopkins HIV Rep. Jul 1999;11(4):1.
Chen, X. et al., "Therapeutic Effect of Radix Astragali On Hypoxia Pulmonary Hypertension In Rats," Zhongguo Zhong Yao Za Zhi. Jul. 1997;22(7):432-4.
Cohn, J.A., "Virology, Immunology, And Natural History Of HIV Infection," J. Nurse Midwifery 1989 Sep.-Oct.;34(5): 242-52.
D'Souza, M.P., et al.,"Current Evidence And Future Directions For Targeting HIV Entry," JAMA, 284, No. 2, 215-222.
Ebata, N. et al., "Saponins From The Root Of Bupleurum Falcatum, " Phytochemistry. 1996 41(3):895-901.
Friend, SCE et al., "Feline Immunodeficiency Virus: Prevalence, Disease Associations and Isolation," Aust. Vet J., 67:237 (1990).
Gardner, M., et al. "Animal Models of AIDS," FASEB Journal 3: 2593 (1989).
Gottlieb, S., "Gap in HIV Infection Widens," BMJ 1998; 317:11.
Harbour et al., "Isolation of a T-Lymphotropic Lentivirus from a Persistently Leucopenic Domesti Cat," Vet Rec, 122:84 (1988).

(Continued)

*Primary Examiner*—Michele C. Flood

(57) ABSTRACT

This invention relates to compositions for the treatment of acquired immunodeficiency diseases, especially human immunodeficiency virus (HIV), and its simian and feline counterparts (simian immunodeficiency virus (SIV), and feline immunodeficiency virus (FIV)), and to methods for their use.

9 Claims, 1 Drawing Sheet

OTHER PUBLICATIONS

Hayashi, T., "Studies On Crude Drugs Originated From Gentianaceous Plants. 1. Determination Of Gentiopicroside, The Bitter Principle Of Gentianae Radix And Gentianae Scabrae Radix," Yakugaku Zasshi. Mar. 1976;96(3):356-61.

Hirsch VM, et al., "Pathogenic Diversity Of Simian Immunodeficiency Viruses," Virus Res. May 1994; 32(2):183-203.

Hu, C.Q. et al., "Anti-AIDS agents, 10. Acacetin-7-O-beta-D-galactopyranoside, an anti-HIV principle from Chrysanthemum morifolium and a structure-activity correlation with some related flavonoids," J Nat Prod. Jan. 1994; 57(1):42-51.

Hu, S. et al., "Influence of medicinal herbs on phagocytosis by bovine neutrophils," Zentralbl Veterinarmed A. Oct. 1992;39(8):593-9.

Ishida et al., "Detection Of Feline T-Lymphotropic Lentivirus (FTLV) Infection In Japanese Domestic Cats," Jpn J Vet Sci, 50:39 (1988).

Izumi, S. et al., "Wide Range Of Molecular Weight Distribution Of Mitogenic Substance(S) In The Hot Water Extract Of A Chinese Herbal Medicine, Bupleurum Chinense," Biol Pharm Bull. Jul. 1997;20(7):759-64.

Johnston, et al., "Present Status and Future Prospects for HIV Therapies," 1993, Science 260, 1286-1293.

Kajimura, K. et al., "Protective Effect Of Astragali Radix By Oral Administration Against Japanese Encephalitis Virus Infection In Mice," Biol Pharm Bull. Sep. 1996;19(9):1166-1169.

Kanbe K., et al., "A CXC Chemokine Receptor, CXCR5/BLR1, Is A Novel And Specific Co-Receptor For Human Immunodeficiency Virus Type 2," Virology Dec. 20 1999; 265(2):264-73.

Kang, J.J. et al., "Modulation Of Microsomal Cytochrome P450 By Scutellariae Radix And Gentianae Scabrae Radix In Rat Liver," Am J Chin Med. 1996;24(1):19-29.

Kim, H.M. et al., "Magnoliae Flos Inhibits Mast Cell-Dependent Immediate-Type Allergic Reactions," Pharmacol Res. Feb. 1999;39(2):107-11.

Kimura, I. et al., "Inhibitory Effects Of Magnoshinin And Magnosalin, Compounds From "Shin-I" (Flos Magnoliae), On The Competence And Progression Phases In Proliferation Of Subcultured Rat Aortic Endothelial Cells, " Jpn J Pharmacol. Sep. 1992;60(1):59-62.

Kimura, I. et al., "Neuromuscular Blocking Action Of Alkaloids From A Japanese Crude Drug "Shin-L" (Flos Magnoliae) In Frog Skeletal Muscle, " Planta Med. May 1983;48(1):43-7.

Kimura, M. et al., "Anti-Inflammatory Effect Of Neolignans Newly Isolated From The Crude Drug "Shin-I" (Flos Magnoliae), " Planta Med. Aug. 1985;(4):291-3.

Kimura, M. et al., "Selective Inhibition By Magnosalin And Magnoshinin, Compounds From "Shin-I" (Flos Magnoliae), Of Adjuvant-Induced Angiogenesis And Granuloma Formation In The Mouse Pouch" , Agents Actions Suppl. 1991; 32:197-201.

Kobayashi, S. et al., "Inhibitory Effect Of Magnosalin Derived From Flos Magnoliae On Tube Formation Of Rat Vascular Endothelial Cells During The Angiogenic Process, " Biol Pharm Bull. Oct. 1996; 19(10):1304-6.

Kobayashi, S. et al., "Inhibitory Effects Of Anti-Rheumatic Drugs Containing Magnosalin, A Compound From 'Shin-l' (Flos Magnoliae), On The Proliferation Of Synovial Cells in Rheumatoid Arthritis Models, "

Kok, L.D. et al., "Activation Of The Anti-Tumor Effector Cells By Radix Bupleuri, " Immunopharmacology. Jun. 1995;30(1):79-87.

Liao, J.F. et al., "Evaluation With Receptor Binding Assay On The Water Extracts Of Ten CNS-Active Chinese Herbal Drugs," Proc Natl Sci Counc Repub China B. Jul. 1995;19 (3):151-8.

Li, G. et al., "Preparation Method And Quality Control Of Compound Daphne Injection" , Zhongguo Zhong Yao Za Zhi. Nov. 1992;17(11):664-5, 702.

Liao, J.F. et al., "Evaluation With Receptor Binding Assay On The Water Extracts Of Ten CNS-Active Chinese Herbal Drugs" , Proc Natl Sci Counc Repub China B. Jul. 1995; 19(3):151-8.

Lin, C.C. et al., "Anatomical And Histological Studies Of Bupleuri Radix," Am J Chin Med. 1991;19(3-4):265-74).

Luckner, M. et al., "Suggestions For The Drug Section Of The DAB 7.5. Radix Gentianae," Pharmazie. Jan. 1965;20 (1):16-9).

Luo, J.P. et al., "Morphological And Histological Studies Of The Chinese Drug Longdan, Radix Gentianae," Yao Xue Xue Bao. Aug. 1987;22(8):619-36.

Martinon, O., et al., "Le Virus de l'Immunodéfience Féline" , Vet Res 1993;24(2):151-8.

Nagasawa, M. et al., "The Geographical Variation Of Essential Oils Of Flos Magnoliae," Yakugaku Zasshi. Apr. 1969;89(4):454-9.

Nakamoto, K. et al., "Effects Of Crude Drugs And Berberine Hydrochloride On The Activities Of Fungi" , J Prosthet Dent. Dec. 1990;64(6):691-4.

Oka, H. et al., "Characterization Of Mitogenic Substances In The Hot Water Extracts Of Bupleuri Radix," Biol Pharm Bull. May 1995;18(5):757-65.

Pedersen, N., et al., "Feline Immunodeficiency Virus Infection," Vet. Immunol. Immunopathol. 21:111-129 (1989).

Pederson et al., "Isolation of a T-Lymphotropic Virus from Domestic Cats with an Immunodeficiency-Like Syndrome" , Science, 235:790 (1987).

Podell, M. et al., "The Feline Model Of Neuroaids: Understanding The Progression Towards AIDS Dementia" , J Psychopharmacol. 2000; 14(3):205-13.

Remington, K. M. et al., "Mutants Of Feline Immunodeficiency Virus Resistant To 3'-Azido-3' - Deoxythymidine," J. Virol. 65: 308-312 (1991).

Rowland-Jones, S., "Long-Term Non-Progression In HIV Infection Clinico Pathological Issues," J. Infection (1999) 38, 67-70.

Sabine et al., "Feline AIDS," Aust Vet Practit, 18:105 (1988).

Smith, R.A., et al., "A Novel Point Mutation In Reverse Transcriptase From Feline Immunodeficiency Virus Confers Resistance To The Combination Of (-)-Beta-2',3'-Dideoxy-3'-Thiacytidine And 3' -Azido-3'-Deoxythymidine," J. Virol. 72: 2335-2340 (1998).

Swinney et al., "Feline T-Lymphotropic Virus (FTLV) (Feline Immunodeficiency Virus Infection) In Cats In New Zealand,"NZ Vet J, 37:41 (1989).

Toda, S. et al., "Inhibitory Effects Of Astragali Radix, A Crude Drug In Oriental Medicines, On Lipid Peroxidation And Protein Oxidative Modification By Copper," J Ethnopharmacol. Dec. 15, 1999;68(1-3):331-333.

Toda, S. et al., "Inhibitory Effects Of Astragali Radix, Crude Drug In Oriental Medicines On Lipid Peroxidation And Protein Oxidative Modification Of Mouse Brain Homogenate By Copper," Phytother Res. Jun. 2000; 14(4): 294-6.

Ukiya, M. et al., "Constituents of Compositae Plants. 2. Triterpene Diols, Triols, and Their 3-O-Fatty Acid Esters from Edible Chrysanthemum Flower Extract and Their Anti-inflammatory Effects," J Agric Food Chem. Jul. 16, 2001;49(7):3187-3197.

Veugelers, P.J., et al., "Differences in the Time form HIV Seroconversion to CD4 Lyphocyte Endpoints and AIDS in Cohots of Homosexual Men," AIDS 1993: 7: 1328-1329.

Wang, D. et al., Protective Effect Of Active Components Extracted From Radix Astragali On Human Erythrocyte Membrane Damages Caused By Reactive Oxygen Species, Zhongguo Zhong Yao Za Zhi. Dec. 1996;21(12):746-8, 763.

Wang, H.K. et al., "Recent Advances In The Discovery And Development Of Flavonoids And Their Analogues As Antihumor And Anti-HIV Agents," Adv Exp Med Biol. 1998;439:191-225.

Willis, A.M., "Feline Leukemia Virus And Feline Immunodeficiency Virus," Vet Clin North Am Small Anim Pract. 2000 Sep;30(5):971-86.

Xi, S. et al., "The Inhibitory Effects Of Radix Astragali On Hypoxic Pulmonary Hypertension Of Rats," Chin Med J (Engl). Oct. 1998;111(10):956-8.

Xu, Z.L. et al., "Studies On The Essential Oils Of Flos Magnoliae," Zhongguo Zhong Yao Za Zhi. May 1989;14(5):294-6, 319.

Xuejiang, W. et al., "Antioxidant Potential Of Qizhu Tang, A Chinese Herbal Medicine, And The Effect On Cerebral Oxidative Damage After Ischemia Reperfusion In Rats," Biol Pharm Bull. May 2001;24(5):558-63.

Yamamoto et al., "Pathogenesis of Experimentally Induced Feline Immunodeficiency Virus Infection In Cats," Am. J. Vet. Res., 8:1246 (1988).

Yarchoan R, et al., "The Immunology of HIV Infection: Implications For Therapy," AIDS Res Hum Retroviruses Jun. 1992;8(6):1023-31.

You, S. et al., "A Clinical Study On Bing Gan Ling Oral Liquid For Treatment Of Hepatitis C," J Tradit Chin Med. Sep. 1998;18(3):209-14.

Zhao, Z.Z. et al., "A New Species And A Variety's New Nomenclature Of The Medicinal Xin-Yi (Flos Magnoliae)," Yao Xue Xue Bao. Oct. 1987;22(10):777-80.

Zhao, Z.Z. et al., "Original botanical study and identification of Flos Magnoliae," Zhong Yao Tong Bao, Jun. 1998;13(6): 3-4, 61.

Zhou, Y.L., "Chrysanthemum morifolium in the treatment of hypertension," Zhong Xi Yi Jie He Za Zhi. Jan. 1987;7(1): 18-20, 4.

http://www.healthlink.com.au.
http://www.holisticat.com/felv arch.html.
http://www.holisticonline.com.
http://www.listservice.net/wellpet/fiv.htm.
http://www.theherbsplace.com/vsc.html.
http://www.walthamusa.com/walthamnavc/Wynn/Wynn/pdf.
http://www.walthamusa.com/walthamnavc/Wynn/Wynn.pdf.
http://www.whiteosepath.com/bodysong/Fiv%20and%20Fel.v.html.
http://www.ancientway.com/catalog/product_info.php?products id=66.
http://www.holistic-online.com/Herbal-Med/_Herbs/h388.htm.

* cited by examiner

COMPOSITIONS FOR THE TREATMENT OF ACQUIRED IMMUNODEFICIENCY DISEASE

CROSS-REFERENCE TO RELATED APPLICATIONS

This application claims priority from U.S. patent application Ser. No. 60/310,831 (filed Aug. 9, 2001), herein incorporated by reference.

FIELD OF THE INVENTION

This invention relates to compositions for the treatment of acquired immunodeficiency diseases, especially human immunodeficiency virus (HIV), and its simian and feline counterparts (simian immunodeficiency virus (SIV), and feline immunodeficiency virus (FIV)), and to methods for their use.

BACKGROUND OF THE INVENTION

In the past 25 years, a new family of viruses capable of causing debilitating immunodeficiency diseases (acquired immunodeficiency diseases, AIDS) in mammals has emerged as a serious global health threat. These viruses, which include the human immunodeficiency virus (HIV), and its simian and feline counterparts (simian immunodeficiency virus (SIV), and feline immunodeficiency virus (FIV)) are composed of single-stranded RNA, and can be transmitted though contact with blood, or through sexual intercourse. Individuals infected with these viruses exhibit a profound collapse of their immune system, and the consequent presentation of secondary opportunistic infections, such as *Candida albicans* oesophagitis, mucocutaneous herpes simplex infection, Pneumocystis carinii-induced pneumonia, cryptosporidial enteritis, etc.

Without treatment, immunodeficiency viral infection is highly lethal. Indeed, AIDS is the leading cause of human death (Chaisson, R. E., "HIV becomes world's leading infectious cause of death," Hopkins HIV Rep. 1999 Jul;11 (4): 1). In certain parts of the world, such as sub-Saharan Africa, at least 10% of all adults are believed to be infected with HIV, with the prevalence in many capital cities believed to be 35% or more (Gottlieb, S., "Gap in HIV infection widens," BMJ 1998;317:11). In the United States, an estimated 800,000 to 900,000 people are currently infected with HIV, with approximately 40,000 new infections occurring each year. Of the more than 700,000 individuals in the United States who were infected with HIV as of December 2000, 58% have died.

Human immunodeficiency virus-1 infects and damages or destroys several types of cells, most importantly helper/inducer (CD4+) lymphocytes. In the majority of infected persons, the loss of CD4+ lymphocytes leads to a progressive reduction in both cell mediated and antibody mediated immunity. Early during infection most adults are asymptomatic, but after several years many develop symptoms representing a moderate degree of immune suppression. Eventually, most of these individuals become susceptible to the life-threatening opportunistic infections and cancers which define the acquired immunodeficiency syndrome (Cohn, J. A., "Virology, immunology, and natural history of HIV infection," J. Nurse Midwifery 1989 September–October;34(5):242–52).

The main cellular target of HIV infection is the CD4+ T cell. CD4+ T-cell titers in most people decline relentlessly throughout the course of HIV infection. In late stages of the disease a change occurs in the phenotype of the virus from non-syncitium-inducing (NSI) isolates of HIV-1 which dominate in primary infection to strains of HIV which are cytopathic and syncitium-inducing (SI) (Rowland-Jones, S., "Long-term Non-progression in HIV Infection Clinico Pathological Issues," J. Infection (1999) 38, 67–70). This change in phenotype also correlates to a change in the chemokine co-receptors used by the virus for entry into CD4+ cells (Veugelers, P. J., et al., "Differences in the Time form HIV Seroconversion to CD4 Lyphocyte Endpoints and AIDS in Cohots of Homosexual Men," AIDS 1993: 7: 1328–1329).

In addition to changes in phenotype, different strains of HIV also target different receptors. G protein-coupled receptors serve as co-receptors in the infection process of human immunodeficiency virus type-1 (HIV-1), type-2 (HIV-2), and SIV. CXC-CKR, CXCR5/BLR1, is a novel co-receptor for HIV-2, but does not appear to function as a receptor for HIV-1 or SIV (Kanbe K., et al., "A CXC chemokine receptor, CXCR5/BLR1, is a novel and specific co-receptor for human immunodeficiency virus type 2," Virology Dec. 20, 1999;265(2):264–73).

HIV is believed to have evolved from its simian counterpart, SIV. The two viruses are genetically very similar, and are transmitted the same way. The disease induced by the SIVsm subtype is, however, remarkably similar to human AIDS. However HIV only causes AIDS in humans, and SIV only causes AIDS in monkeys. The SIV family is, however, a diverse group of viruses that vary considerably in pathogenesis and virulence in their natural host species (macaques). The pathogenesis of SIVsm (and other viruses) in macaques offers an relevant animal model for pathogenesis and vaccine trials, the interactions of these viruses in their natural host, and virus-, or host-specific effects (U.S. Pat. No. 6,017,536 (Barney, et al.; Hirsch VM, et al., "Pathogenic diversity of simian immunodeficiency viruses," Virus Res 1994 May;32(2):183–203).

Feline immunodeficiency virus (FIV, formerly called feline T lymphotropic lentivirus (Pederson et al., Science, 235:790 (1987)), has been identified in the United States, the United Kingdom (Harbour et al., Vet Rec, 122:84 (1988)), Japan (Ishida et al., Jpn J Vet Sci, 50:39 (1988)), Australia (Sabine et al., Aust Vet Practit, 18:105 (1988)), and New Zealand (Swinney et al., NZ Vet J, 37:41 (1989)). The virus appears to be spread by horizontal transmission, predominantly by bite wounds (Yamamoto et al., Am. J. Vet. Res., 8:1246 (1988); Friend et al., Aust. Vet J., 67:237 (1990). FIV is a typical retrovirus that preferentially replicates in feline T lymphoblastoid cells and is the causative agent of a cat disease with features similar to those of HIV-induced human AIDS (Pedersen, N., et al., Science 235: 790 (1987); U.S. Pat. No. 5,665,592 (Tompkins, et al.)). HIV-1 and FIV belong to the lentivirus subfamily of retroviruses, have similar morphology, protein composition, and reverse transcriptases (RT) that exhibit $Mg^{2+}$-dependency (Pedersen, N., et al., Science 235: 790 (1987); Pedersen, N., et al., Vet. Immunol. Immunopathol. 21: 111 (1989)). Both HIV and FIV display tropism for T lymphocytes and monocytes and are capable of inducing these cells to form syncytia. (Brunner, D., et al., J. Virol. 63: 5483 (1989); Gardner, M., et al. FASEB Journal 3: 2593 (1989)). FIV is reviewed by Willis, A. M. ("Feline leukemia virus and feline immunodeficiency virus," Vet Clin North Am Small Anim Pract. 2000 September;30(5):971–86); Podell, M. et al. ("The feline model of neuroAIDS: understanding the progression towards AIDS dementia," J Psychopharmacol. 2000;14(3):205–13); and Bogers, W. M. et al. ("Developments in preclinical AIDS vaccine efficacy models," AIDS. 2000;14 Suppl 3:S141–51).

While the overall genetic organization of FIV is similar to that of HIV, the reduced complexity of FIV's regulatory open reading frames suggests that FIV may be closer to ungulate lentiviruses than to primate lentiviruses.

FIV infects both $CD4^+$ and $CD8^+$ T lymphocytes as well as feline B lymphocytes and macrophages. In addition, the FIV cellular receptor does not appear to be mostly constituted by the feline CD4 differentiation antigen (Martinon, O., et al., "URA-INRA, Immunopathologie cellulaire et moleculaire (IPCM)," Vet Res 1993;24(2):151–8). U.S. Pat. No. 5,648,209, (Avrameas, et al.) describes the feline immunodeficiency virus (FIV), and the use of FIV peptide fragments as diagnostic reagents. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline CD4+ peripheral blood lymphocytes, a reduction in the CD4:CD8 cell ratio and, in some cases, an increase in CD8-bearing lymphocytes. Cats with full blown Feline AIDS have an average life expectancy of no more than six months to a year. No effective treatment for FIV has yet been defined. U.S. Pat. No. 6,254,872 (Yamamoto) discusses FIV-vaccines. U.S. Pat. No.6,228,608 (Young et al.) discusses the use of viral proteins as antigens to provide a therapy for FIV infection.

It is known that antiretroviral drugs can induce immunologic improvement in patients with acquired immunodeficiency syndrome (AIDS) and other manifestations of immunovirus infection. Significant progress has been made in the development of antiretroviral therapy (ART) to block retroviral transcription and assembly. Sixteen licensed antiretroviral drugs are in use that target HIV-1 proteins such as Vpr, Tat, Rev, Vif, Nef, Env, Gag, Vpu. Antiretroviral therapies include nucleoside analogues (NA), protease inhibitors, non-nucleoside reverse transcriptase inhibitors (NNRTI), nucleoside analogs, and combination therapies employing one or more of therapies listed above). Other strategies for inhibiting retroviral infection are discussed by Johnston, et al., 1993, Science 260, 1286–1293, and by Franzusoff, et al. (U.S. Pat. No. 5,691,183).

The use of alternative treatments and medicinal herbs has been suggested for the treatment of feline acquired immunodeficiency disease (see, e.g., Garlic, Goldenseal, Cats claw, Ambrotose, Acemannan (abstract of Aloe), Essaic Tea, Baypamun, Felovite II with Taurine, Immuplex/Livaplex/Thymex/Cataplex AC/Pneumotrophin PMG Echinacea C/Immuplex/Congaplex, Vitamin C, Colloidal silver, Co enzyme Q10, MGN-3, Flax Seed Oil, Vanilla flavoring, Liquid Chlorophyll, Ester-C powder, Bone Meal powder, Acidophilus powder, Beta Carotene, Parsley, Vitamin E, Brewers Yeast, thymus hormone, Melissa, Hypericum, Lomatium, Turmeric, and Momordica, (see, http://www.holisticat.con/felv arch.html; http://www.listservice.net/wellpet/fiv.htm; http://www.whiterosepath.com/bodysong/Fiv%20and%20FeLV.html; http://wWw.walthamusa.com/walthamnavc/Wynn/Wynn.pdf). The use of alternative medicaments for FIV is discussed by Wynn, S. G. ("Integrative Approaches to Feline Viral Diseases." http://www.walthamusa.com/walthamnavc/Wynn/Wynn.pdf).

An herbal formulation ("VS-C;" http://www.theherbsplace.com/vsc.html) is sold as a treatment for FIV. The ingredients of VS-C are: Dandelion Root, Purslane Herb, Indigo, Herb & Root (contains indirubin), Thlaspi, Buplbu-rum Root, Scute Root, Pinellia Rhizome, Ginseng Root, Cinnamon Twig, and Licorice Root.

Despite such progress, no fully successful therapy for acquired immunodeficiency diseases has yet been identified. In light of the substantial morbidity and mortality associated with immunodeficiency virus infection, a need exists for improved therapies for treating viral-induced immunodeficiency disease and/or preventing the proliferation of immunodeficiency viruses. Despite the therapeutic advances made by antiretroviral therapies, problems of drug resistance, latent viral reservoirs, and drug-induced toxic effects that compromise effective viral control point to a need for new classes of anti-HIV drugs with different modes of action. (D'Souza, M. P., et al., "Current Eviidence and Future Directions for Targeting HIV Entry," JAMA, Jul. 12, 2000—Vol. 284, No. 2) (Yarchoan R, et al., "The immunology of HIV infection: implications for therapy," AIDS Res Hum Retroviruses 1992 June;8(6):1023–31). The present invention is directed to such needs.

SUMMARY OF THE INVENTION

This invention relates to compositions for the treatment of acquired immunodeficiency diseases, especially human immunodeficiency virus (HIV), and its simian and feline counterparts (simian immunodeficiency virus (SIV), and feline immunodeficiency virus (FIV)), and to methods for their use.

In detail, the invention concerns compositions comprising the five herbs Radix *Gentianae Longdancao,* Fructus *Xanthii Sibirici,* Radix *Bupleuri,* Radix *Astragali,* and *Chrysanthemum Morifolium,* or an extract of said herbs. The invention particularly concerns such a composition wherein the herbs or extract thereof comprises by weight percent: 5–80% Radix *Gentianae Longdancao;* 5–80% Fructus *Xanthii Sibirici;* 5–80% Radix *Bupleuri,* 1–40% Radix *Astragali;* and 1–40% *Chrysanthemum Morifolium,* and more particularly concerns such a composition wherein the herbs or extract thereof comprises by weight percent: 10–70% Radix *Gentianae Longdancao;* 10–70% Fructus *Xanthii Sibirici;* 10–70% Radix *Bupleuri,* 1–30% Radix *Astragali;* and 1–30% *Chrysanthemum Morifolium.*

The invention also concerns a pharmaceutical composition for the treatment of a disease state or condition associated with immunodeficiency virus infection in a mammal, the composition comprising a therapeutically effective amount of the herbs Radix *Gentianae Longdancao,* Fructus *Xanthii Sibirici,* Radix *Bupleuri,* Radix *Astragali,* and *Chrysanthemum Morifolium,* or an extract of the herbs. The invention particularly concerns such a pharmaceutical composition wherein the therapeutically effective amount of herbs or extract thereof comprises by weight percent: 5–80% Radix *Gentianae Longdancao;* 5–80% Fructus *Xanthii Sibirici;* 5–80% Radix *Bupleuri,* 1–40% Radix *Astragali;* and 1–40% *Chrysanthemum Morifolium,* and more particularly concerns such a composition wherein said therapeutically effective amount of herbs or extract thereof comprises by weight percent: 10–70% Radix *Gentianae Longdancao;* 10–70% Fructus *Xanthii Sibirici;* 10–70% Radix *Bupleuri,* 1–30% Radix *Astragali;* and 1–30% *Chrysanthemum Morifolium.*

The herbal compositions may additionally optionally contain *Flos Magnoliae,* for example at a weight percent of 1–40%, and more particularly 1–30%.

The invention particularly concerns the embodiments of such pharmaceutical compositions wherein the mammal is a human, the disease state or condition is AIDS, and the immunodeficiency virus is HIV, or wherein the mammal is a feline, the disease state or condition is AIDS, and the immunodeficiency virus is FIV.

The invention particularly concerns the embodiments of such pharmaceutical compositions wherein the composition is administered by a parenteral, intramuscular, subcutaneous, oral, sublingual, intravenous, intravaginal, intraural, intraocular, nasal, bronchial, transdermal or topical route.

The invention also provides a method for treating a disease state or condition associated with immunodeficiency virus infection in a mammal, the method comprising administering a therapeutically effective amount of a pharmaceutical composition comprising a therapeutically effective amount of the herbs Radix *Gentianae Longdancao*, Fructus *Xanthii Sibirici*, Radix *Bupleuri*, Radix *Astragali*, and *Chrysanthemum Morifolium*, or an extract thereof.

The invention particularly concerns such method wherein said therapeutically effective amount of herbs or extract thereof comprises by weight percent: 5–80% Radix *Gentianae Longdancao;* 5–80% Fructus *Xanthii Sibirici;* 5–80% Radix *Bupleuri*, 1–40% Radix *Astragali;* and 1–40% *Chrysanthemum Morifolium,* and more particularly concerns such a composition wherein said therapeutically effective amount of herbs or extract thereof comprises by weight percent: 10–70% Radix *Gentianae Longdancao;* 10–70% Fructus *Xanthii Sibirici;* 10–70% Radix *Bupleuri,* 1–30% Radix *Astragali;* and 1–30% *Chrysanthemum Morifolium.*

The invention also provides the embodiment of such methods wherein the mammal is a human, the disease state or condition is AIDS, and the immunodeficiency virus is HIV, wherein the mammal is a feline, the disease state or condition is AIDS, and the immunodeficiency virus is FIV, and wherein the mammal is a simian, the disease state or condition is AIDS, and the immunodeficiency virus is SIV.

The invention also provides the embodiment of such methods wherein the pharmaceutical composition is administered by a parenteral, intramuscular, subcutaneous, oral, sublingual, intravenous, intravaginal, intraural, intraocular, nasal, bronchial, transdermal or topical route.

DESCRIPTION OF THE PREFERRED EMBODIMENTS

Figure 1:
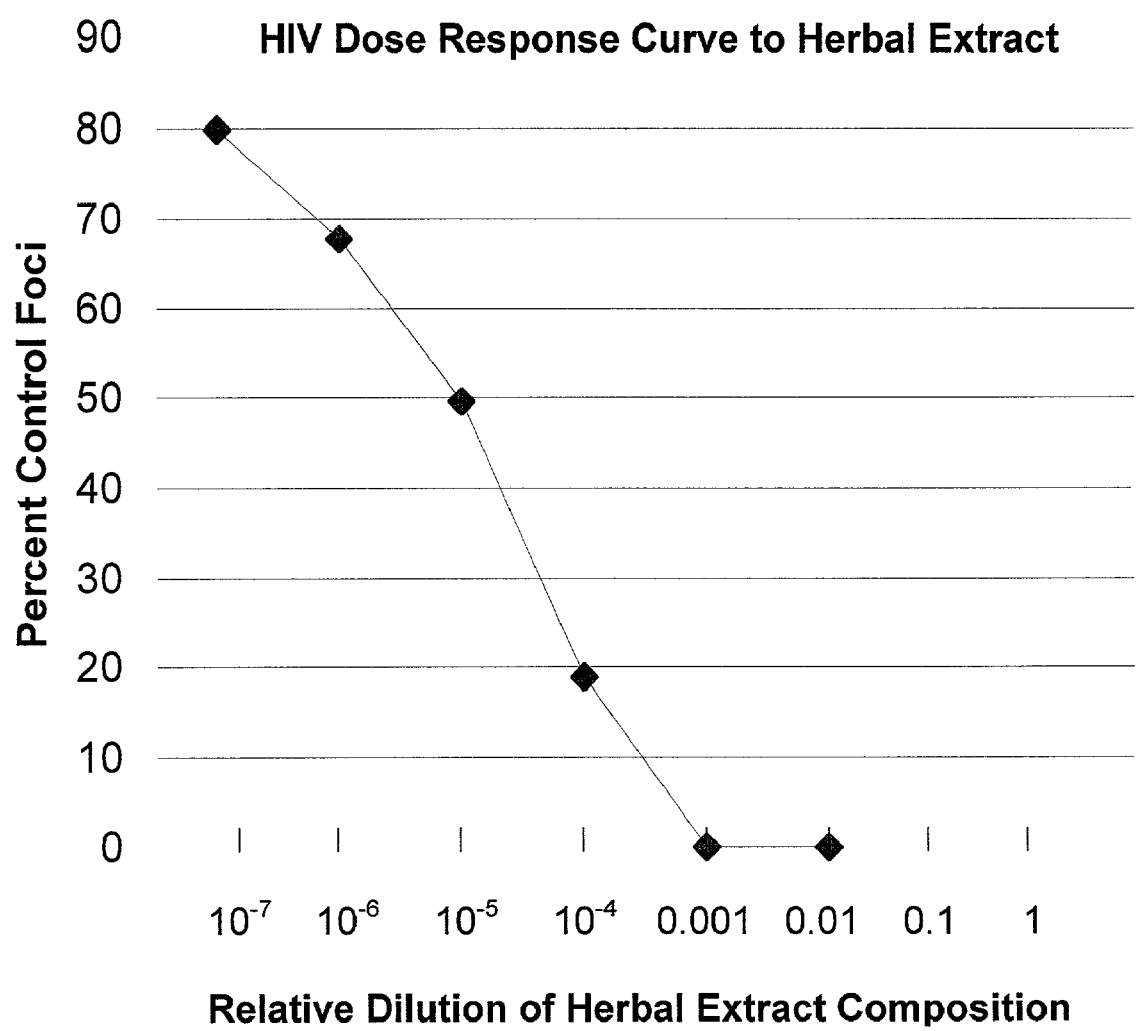
FIG. 1 shows the efficacy of the herbal compositions of the present invention in attenuating the propagation of HIV.

The invention concerns herbal compositions that are capable of inhibiting the propagation or infectivity of viruses, such as HIV, SIV or FIV that cause immunodeficiency diseases in mammals. The preferred compositions of the present invention comprise a combination of five herbs or extracts thereof: Radix *Gentianae Longdancao*, Fructus *Xanthii Sibirici*, Radix *Bupleuri*, Radix *Astragali*, and *Chrysanthemum Morifolium.* More preferably the composition will contain (by weight percent): 5–80% Radix *Gentianae Longdancao;* 5–80% Fructus *Xanthii Sibirici;* 5–80% Radix *Bupleuri,* 1–40% Radix *Astragali;* and 1–40% *Chrysanthemum Morifolium.* Most preferably, the composition will contain (by weight percent): 10–70% Radix *Gentianae Longdancao;* 10–70% Fructus *Xanthii Sibirici;* 10–70% Radix *Bupleuri,* 1–30% Radix *Astragali;* and 1–30% *Chrysanthemum Morifolium.* In the most preferred embodiment, for inhibiting the propagation or infectivity of HIV, such herbal composition will comprise the Human Immune Virtuous Herbal™ (HIV Herbal™) product obtainable from Zen-Tech, Inc. (Los Angeles, Calif.). In the most preferred embodiment, for inhibiting the propagation or infectivity of FIV, such herbal composition will comprise Feline Immune Virtuous Herbal™ (FIV Herbal™) product obtainable from Zen-Tech, Inc. (Los Angeles, Calif.).

*Flos Magnoliae* (especially at concentrations of weight percent 1–40% or 1–30%) may be additionally optionally included.

Radix *Gentianae Longdancao* is described in the scientific literature (Kang, J. J. et al., "Modulation of microsomal cytochrome P450 by Scutellariae Radix and *Gentianae scabrae* Radix in rat liver," Am J Chin Med. 1996;24(1): 19–29; Liao, J. F. et al., "Evaluation with receptor binding assay on the water extracts of ten CNS-active Chinese herbal drugs," Proc Natl Sci Counc Repub China B. 1995 July;19 (3):151–8; Li, G. et al., "Preparation method and quality control of compound Daphne injection," Zhongguo Zhong Yao Za Zhi. 1992 November;17(11):664–5, 702; Luo, J. P. et al., "Morphological and histological studies of the Chinese drug longdan, radix *Gentianae*," Yao Xue Xue Bao. 1987 Aug;22(8):619–36; Hayashi, T., "Studies on crude drugs originated from Gentianaceous plants. I. Determination of gentiopicroside, the bitter principle of *Gentianae* radix and *Gentianae scabrae* radix," Yakugaku Zasshi. 1976 March;96(3):356–61; Luckner, M. et al., "Suggestions for the drug section of the DAB 7.5. Radix *Gentianae,*" Pharmazie. 1965 January;20(1):16–9).

Information regarding Fructus *Xanthii Sibirici* can be found at http://www.holisticonline.com and http://www.healthlink.com.au, and elsewhere on the Internet.

Radix *Bupleuri* has been described in the scientific literature (Ahn, B. Z. et al., "Inhibitory effect of *bupleuri* radix saponins on adhesion of some solid tumor cells and relation to hemolytic action: screening of 232 herbal drugs for anti-cell adhesion," Planta Med. 1998 April;64(3):220–4; Izumi, S. et al., "Wide range of molecular weight distribution of mitogenic substance(s) in the hot water extract of a Chinese herbal medicine, *Bupleurum chinense*," Biol Pharm Bull. 1997 July;20(7):759–64; Ebata, N. et al., "Saponins from the root of *Bupleurum falcatum,*" Phytochemistry. 1996 February;41(3):895–901; Kok, L. D. et al., "Activation of the anti-tumor effector cells by Radix *bupleuri,*" Immunopharmacology. 1995 June;30(1):79–87; Oka, H. et al., "Characterization of mitogenic substances in the hot water extracts of *bupleuri* radix," Biol Pharm Bull. 1995 May;18 (5):757–65; Hu, S. et al., "Influence of medicinal herbs on phagocytosis by bovine neutrophils," Zentralbl Veterinarmed A. 1992 October;39(8):593–9; Lin, C. C. et al., "Anatomical and histological studies of *Bupleuri* radix," Am J Chin Med. 1991;19(3–4):265–74).

Radix *Astragali* has also been described in the scientific literature (Xuejiang, W. et al., "Antioxidant potential of qizhu tang, a chinese herbal medicine, and the effect on cerebral oxidative damage after ischemia reperfusion in rats," Biol Pharm Bull. 2001 May;24(5):558–63; Xi, S. et al., "The inhibitory effects of Radix *Astragali* on hypoxic pulmonary hypertension of rats," Chin Med J (Engl). 1998 October; 111(10):956–8; Chen, X. et al., "Therapeutic effect of radix *Astragali* on hypoxia pulmonary hypertension in rats," Zhongguo Zhong Yao Za Zhi. 1997 Jul;22(7):432–4; Kurashige, S. et al., "Effects of astragali radix extract on carcinogenesis, cytokine production, and cytotoxicity in mice treated with a carcinogen, N-butyl-N'-butanolnitrosoamine," Cancer Invest. 1999;17(1):30–5; Toda, S. et al., "Inhibitory effects of *astragali* radix, crude drug in Oriental medicines on lipid peroxidation and protein oxidative modification of mouse brain homogenate by copper,"

Phytother Res. 2000 June;14(4):294–6; Toda, S. et al., "Inhibitory effects of *Astragali* Radix, a crude drug in Oriental medicines, on lipid peroxidation and protein oxidative modification by copper," J Ethnopharmacol. 1999 December 15;68(1–3):331–3; You, S. et al., "A clinical study on bing gan ling oral liquid for treatment of hepatitis C," J Tradit Chin Med. 1998 September;18(3):209–14; Wang, D. et al., Protective effect of active components extracted from radix *Astragali* on human erythrocyte membrane damages caused by reactive oxygen species," Zhongguo Zhong Yao Za Zhi. 1996 Dec;21(12):746–8, 763; Kajimura, K. et al., "Protective effect of *astragali* radix by oral administration against Japanese encephalitis virus infection in mice," Biol Pharm Bull. 1996 September;19(9): 1166–9).

*Chrysanthemum Morifolium* has also been described in the scientific literature, particularly with regard to asserted anti-HIV activity (Ukiya, M. et al., "Constituents of Compositae Plants. 2. Triterpene Diols, Triols, and Their 3-O-Fatty Acid Esters from Edible *Chrysanthemum* Flower Extract and Their Anti-inflammatory Effects," J Agric Food Chem. 2001 July 16;49(7):3187–3197; Wang, H. K. et al., "Recent advances in the discovery and development of flavonoids and their analogues as antitumor and anti-HIV agents," Adv Exp Med Biol. 1998;439:191–225; Hu, C. Q. et al., "Anti-AIDS agents, 10. Acacetin-7-O-beta-D-galactopyranoside, an anti-HIV principle from *Chrysanthemum morifolium* and a structure-activity correlation with some related flavonoids," J Nat Prod. 1994 January;57(1):42–51; Zhou, Y.L., "*Chrysanthemum morifolium* in the treatment of hypertension," Zhong Xi Yi Jie He Za Zhi. 1987 January;7 (1):18–20, 4).

*Flos Magnoliae* has been described in the scientific literature (Kim, H. M. et al., "*Magnoliae Flos* inhibits mast cell-dependent immediate-type allergic reactions," Pharmacol Res. 1999 Feb;39(2):107–11; Kobayashi, S. et al., "Inhibitory effects of anti-rheumatic drugs containing magnosalin, a compound from 'Shin-i' (*Flos magnoliae*), on the proliferation of synovial cells in rheumatoid arthritis models," Immunopharmacology. 1998 May;39(2):139–47; Kobayashi, S. et al., "Inhibitory effect of magnosalin derived from *Flos magnoliae* on tube formation of rat vascular endothelial cells during the angiogenic process," Biol Pharm Bull. 1996 October;19(10):1304–6; Kimura, I. et al., "Inhibitory effects of magnoshinin and magnosalin, compounds from "Shin-i" (*Flos magnoliae*), on the competence and progression phases in proliferation of subcultured rat aortic endothelial cells," Jpn J Pharmacol. 1992 September; 60(1):59–62; Kimura, M. et al., "Selective inhibition by magnosalin and magnoshinin, compounds from "Shin-i" (*Flos magnoliae*), of adjuvant-induced angiogenesis and granuloma formation in the mouse pouch," Agents Actions Suppl. 1991;32: 197–201; Nakamoto, K. et al., "Effects of crude drugs and berberine hydrochloride on the activities of fungi," J Prosthet Dent. 1990 December;64(6):691–4; Xu, Z. L. et al., "Studies on the essential oils of *Flos Magnoliae*," Zhongguo Zhong Yao Za Zhi. 1989 May;14(5):294–6, 319; Zhao, Z. Z. et al., "Original botanical study and identification of *Flos Magnoliae*," Zhong Yao Tong Bao. 1988 June; 13(6):3–4, 61; Zhao, Z. Z. et al., "A new species and a variety's new nomenclature of the medicinal xin-yi (*Flos Magnoliae*)," Yao Xue Xue Bao. 1987 October;22(10): 777–80; Kimura, M. et al., "Anti-inflammatory effect of neolignans newly isolated from the crude drug "Shin-i" (*Flos Magnoliae*)," Planta Med. 1985 August;(4):291–3; Kimura, I. et al., "Neuromuscular blocking action of alkaloids from a Japanese crude drug "Shin-1" (*Flos Magnoliae*) in frog skeletal muscle," Planta Med. 1983 May;48(1):43–7; Nagasawa, M. et al., "The geographical variation of essential oils of *Flos Magnoliae*," Yakugaku Zasshi. 1969 April; 89(4):454–9).

Each herbal ingredient is made into powder form. The powdered forms are then dissolved in water by heating for about 10 minutes at 250° F. to form a syrup. Such syrup can, of course, be further compounded into other medicament forms, if desired. The product of such process(es) comprise (s) the preferred herbal compositions of the present invention.

The herbal compositions of the present invention may be employed as pharmaceutical agents to effect the treatment of disease states and conditions associated with immunodeficiency virus infection. Accordingly, in another embodiment, the invention is drawn to pharmaceutical compositions comprising therapeutically effective amounts of the herbal compositions of the invention, their active agents or pharmaceutically acceptable salts or formulations thereof.

The term "treatment" as used herein covers any treatment of a disease state associated with immunodeficiency virus infection in a mammal, and particularly in a human, cat or simian and includes: (i) preventing the disease state or condition from occurring in a subject which may be predisposed to the disease state but has not yet been diagnosed as having it; (ii) inhibiting the disease state or condition, i.e. arresting its development; or (iii) relieving the disease state or condition, i.e. causing its regression or the amelioration of any of its symptoms.

By the term "disease states and conditions associated with immunodeficiency virus infection" as used herein is intended to cover all disease states which are generally acknowledged in the art to be caused or clinically dependent upon immunodeficiency virus infection or propagation, and those disease states which have been found to be usefully prevented or alleviated by treatment with the specific compounds of the invention. These include, by way of illustration and not limitation, AIDS, ARC, immunodeficiency virus propagation or infectivity, etc., immunodeficiency virus-associated dementia, etc. In particular, the invention may be used to provide therapy for the disease state associated with acquired immunodeficiency diseases such as human, feline or simian AIDS.

As used herein, the term "therapeutically effective amount" refers to that amount of the herbal compositions of the present invention which, when administered to a mammal in need thereof, is sufficient to effect treatment (as defined above), for example, as an inhibitor of immunodeficiency virus propagation or infection or transmission, etc. The amount that constitutes a "therapeutically effective amount" will vary depending on the composition provided, the disease state or condition being treated, and its severity, and the mammalian species to receive the therapy, its weight, age, etc. Such amount may be determined routinely by one of ordinary skill in the art with regard to contemporary knowledge and to this disclosure.

As used herein a "pharmaceutically acceptable salt" is intended to mean a salt that retains the biological effectiveness and properties of the compositions of the invention and which are not biologically or otherwise undesirable. Salts may be derived from acids or bases. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The pharmaceutical compositions can comprise one or more excipients (e.g., buffer, protein, detergent, lipid, a water-soluble polymer, preservative, etc.) and may comprise one or more addition active pharmaceutical ingredients, such as one or more additional bioactive agents. In one embodiment of the invention, the pharmaceutical compositions of the invention will be administered using a drug delivery system. Such drug delivery systems may include formulations that provide site-specific release, or that enhance protection for the intestinal mucosa, etc. Suitable formulations include: dry powder formulations, delivery via particles, liposome encapsulation, transdermal patches, electrically aided transport (electroporation therapy), etc. The drug delivery system may comprise agents to facilitate the controlled release of the herbal compositions of the invention. Such agents may include: poly(urethanes), poly(siloxanes), poly(methyl methacrylate), poly(vinyl alcohol) for hydrophilicity and strength, poly(ethylene), poly(vinyl pyrrolidone), poly(2-hydroxy ethyl methacrylate), poly(n-vinyl pyrrolidone), poly(methyl methacrylate), poly(vinyl alcohol), poly(acrylic acid), polyacrylamide, poly(ethyleneco-vinyl acetate), poly(ethylene glycol), poly (methacrylic acid), etc. In a further preferred embodiment, biodegradeable polymers may be employed to facilitate drug delivery. Such biodegradeable polymers incude polylactides (PLA), polyglycolides (PGA), poly(lactide-co-glycolides) (PLGA), polyanhydrides, and polyorthoesters. Drug delivery devices, and methods for their use are described in U.S. patents; U.S. Pat. Nos. 6,072,041; 6,041,253; 6,018,678; 6,017,318; 6,002,961; 5,879,712; 5,849,331; 5,792,451; 5,783,212; 5,766,633; 5,759,566; 5,690,954; 5,681,811; 5,654,000; 5,641,511; 5,438,040; 4,810,499; and 4,659,558.

Administration can be via any accepted systemic or local route, for example, via parenteral, intramuscular, subcutaneous, oral or sublingual (particularly for infant and animal formulations), intravenous, intravaginal, intraural, intraocular, nasal, bronchial inhalation (i.e., aerosol formulation), transdermal or topical routes, in the form of solid, semi-solid or liquid or aerosol dosage forms, such as, for example, tablets, pills, gel caps, capsules, powders, liquids, solutions, emulsion, injectables, suspensions, suppositories, aerosols or the like. The polymer-modified synthetic erythropoiesis stimulating proteins of the invention can also be administered in sustained or controlled release dosage forms, including depot injections, osmotic pumps, pills, transdermal (including electrotransport) patches, and the like, for the prolonged administration of the polypeptide at a predetermined rate, preferably in unit dosage forms suitable for single administration of precise dosages. The compositions will include a conventional pharmaceutical carrier or excipient and a protein antagonist or agonist of the invention and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

Although more of the composition may be required, oral administration can be used to deliver the herbal compositions of the invention using a convenient daily dosage regimen, which can be adjusted according to the degree of prevention desired or in the alleviation of the affliction. For such oral administration, a pharmaceutically acceptable, non-toxic composition is formed by the incorporation of any of the normally employed excipients, such as, for example, pharmaceutical grades of mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, dispersible tablets, pills, capsules, powders, sustained release formulations and the like. Oral formulations are particularly suited for treatment of gastrointestinal disorders. Oral bioavailablity for general systemic purposes can be adjusted by utilizing excipients that improve uptake to systemic circulation, such as formulation comprising acetylated amino acids. See, e.g., U.S. Pat. Nos. 5,935,601 and 5,629,020.

Oral compositions may take the form of a lozenge, capsule, pill or tablet and thus the composition will contain, along with the herbal composition, a diluent such as lactose, sucrose, dicalcium phosphate, and the like; a disintegrant such as croscarmellose sodium, starch or derivatives thereof; a lubricant such as magnesium stearate and the like; and a binder such as a starch, polyvinylpyrrolidone, gum acacia, gelatin, cellulose and derivatives thereof, and the like.

Liquid pharmaceutically administrable compositions (such as a syrup, elixir, etc.) can, for example, be prepared by dissolving, dispersing, etc. the herbal composition of the invention and optional pharmaceutical adjuvants in a carrier, such as, for example, water, saline, aqueous dextrose, glycerol, glycols, ethanol, preservatives and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see Remington's Pharmaceutical Sciences, Mack Publishing Company, Easton, Pa. The composition or formulation to be administered will, in any event, contain a quantity of the active ingredient in an amount effective to prevent or alleviate the symptoms of the subject being treated. For oral administration to infants, a liquid formulation (such as a syrup or suspension) is preferred.

The compositions of the present invention may be administered parenterally. Parenteral administration is generally characterized by injection, either subcutaneously, intramuscularly or intravenously, and can include intradermal or intraperitoneal injections as well as intrasternal injection or infusion techniques. Injectables can be prepared in conventional forms, either as liquid solutions or suspensions, solid forms suitable for solution or suspension in liquid prior to injection, as emulsions or in biocompatible polymer-based microspheres (e.g., liposomes, polyethylene glycol derivatives, poly(D,C)lactide and the like). Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, protein carriers and the like, such as for example, sodium acetate, polyoxyethylene, sorbitan monolaurate, triethanolamine oleate, cyclodextrins, serum albumin etc. The composition may be administered as a bolus injection or as a continuous infusion.

All publications and patents mentioned in this specification are herein incorporated by reference to the same extent as if each individual publication or patent application was specifically and individually indicated to be incorporated by reference. Having now generally described the invention, the same will be more readily understood through reference to the following examples, which are provided by way of illustration, and are not intended to be limiting of the present invention, unless specified.

Having now generally described the invention, the same will be more readily understood through reference to the following examples, which are provided by way of illustration, and are not intended to be limiting of the present invention, unless specified.

EXAMPLE 1

Clinical Efficacy of Herbal Product

In order to assess the clinical efficacy of the herbal compositions of the present invention, the cytotoxicity of Human Immune Virtuous Herbal™ (HIV Herbal™) (Zen-Tech, Inc., Los Angeles, Calif.) and Feline Immune Virtuous Herbal™ (FIV Herbal™) (Zen-Tech, Inc. (Los Angeles, Calif.). Both HIV Herbal™ and FIV Herbal™ were prepared as a syrup by dissolving their constituent powdered herbals (Radix *Gentianae Longdancao;* Fructus *Xanthii Sibirici;* Radix *Bupleuri,* Radix *Astragali;* and *Chrysanthemum Morifolium*) in water by heating for about 10 minutes at 250° F. to form a syrup.

The cytotoxicity and anti-viral activity of such composition was evaluated by researchers of the University of California, Davis, School of Veterinary Medicine, as described below.

Cytotoxicity

The FIV Herbal™ composition was evaluated for cytotoxicity using Crandell feline kidney (CrFK) cells. A 50% inhibition of cell growth was observed at a 250-fold dilution of the composition, and slight inhibition (about 10%) was observed at a 500-fold dilution of the composition. No effects on cell growth or viability were observed at 1000-fold or greater dilutions of the composition.

A similar evaluation for HIV Herbal™ was conducted using HeLa H1-JC37 cells that are used in assays for SIV. These cells are HeLa cells that have been engineered to express CD4 and CXCR5 receptors, making them susceptible to all isolates of HIV and SIV. Equivalent results were obtained. However, when the composition was provided to the cells without prior filtration, intracellular inclusions were noticed. These inclusions were substantially reduced by filtration, which removed particulate material.

The results of these experiments indicate that the compositions of the present invention are non-toxic to cells.

Antiviral Activity

A) FIV

Anti-FIV activity was determined using a focus infectivity assay. In brief, inhibition of FIV infection was quantified by a focal infectivity assay (Remington, K. M. et al., "Mutants of feline immunodeficiency virus resistant to 3'-azido-3' deoxythymidine," J. Virol. 65: 308–312 (1991), and Smith, R. A., et al., "A novel point mutation in reverse transcriptase from feline immunodeficiency virus confers resistance to the combination of (−)-beta-2',3'-dideoxy-3'-thiacytidine and 3'-azido-3'-deoxythymidin," J. Virol. 72: 2335–2340 (1998)). Resulting data were plotted as the percentage of control foci (no anti-imunodeficiency virus composition) versus inhibitor concentration. Concentrations of composition required to inhibit focus formation by 50% (50% effective concentrations [EC50s]) were obtained directly from the linear portion of these plots by using a computer-generated regression line (Remington, K. M. et al., "Mutants of feline immunodeficiency virus resistant to 3'-azido-3'-deoxythymidine," J. Virol. 65: 308–312 (1991)). Within an experiment, each value represents the mean of four determinations. Results from three or more independent experiments were used to derive the EC50±standard error.

The following experiments were performed:
1) Virus was added first and then drug dilutions were added after a 2-hr adsorption period;
2) Cells were preincubated with drug dilutions for 2 hr prior to infection and appropriate drug dilutions maintained throughout infection; and
3) Virus and drug dilutions were added simultaneously and appropriate drug dilutions maintained throughout infection.

In each experiment 6 different concentrations of herbal composition (dilutions of the composition) were tested and the concentrations required to inhibit virus replication by 50% and by 90% were determined from dose-response plots.

The results revealed that FIV replication was inhibited by 50% with a 10,000-fold dilution of the FIV Herbal™. An inhibition of 90% was observed at approximately 2,000-fold dilutions. The order of virus and composition addition did not matter. Similar results were obtained when dilutions of composition were added 2 hr prior to, 2 hr after or at the same time as virus.

B) SIV and HIV

Anti-SIV and anti-HIV activity was determined using a focal infectivity assay developed for SIV and HIV-1. The assay is similar to the above-described assay for FIV except that HeLa H1-JC-37 cells are employed, and anti-SIV antibodies are used for the immunostaining of SIV foci.

In experiments with SIV, dilutions of HIV Herbal™ were added to cells that had been preincubated with SIV (for two hours) to permit adsorption. Inhibition of SIV replication by 50% was observed at a 10,000-fold dilution and SIV inhibition of 90% was observed at a 1,000-fold dilution.

Experiments with HIV, demonstrated that HIV-1 was inhibited by the HIV Herbal™ product to about the same extent as FIV and SIV, or slightly better (FIG. 1). In FIG. 1, the relative number of viral foci (foci arising from treated cells divided by foci arising from untreated cells) are shown as a function of the relative concentration of herbal composition (dilution factor). Inhibition of HIV replication by 50% was achieved with dilutions of 20,000-fold to 100,000-fold.

This indicates that HIV may be more sensitive to the compositions of the present invention than either FIV or SIV. In two experiments a 1,000-fold dilution of the compositions of the present invention completely inhibited HIV replication. No cell toxicity was observed with the dilutions (1,000-fold or greater).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An antiviral composition comprising effective amounts of extracts of the five herbs: Radix *Gentianae Longdancao* (*Gentianae longdancao*), Fructus *Xanthii Sibirici* (*Xanthii sibirici*), Radix *Bupleuri* (*Bupleurum chinense*), Radix *Astragali* (*Astralagus membranaceus*), and *Chrysanthemum Morifolium* (*Chrysanthemum morifolium*), said composition having a therapeutic index of between at least 80 and 400.

2. The composition of claim 1, wherein said herbal extracts comprise by weight percent: 5–80% Radix *Gentianae Longdancao* (*Gentianae longdancao*); 5–80% Fructus *Xanthii Sibirici* (*Xanthii sibirici*); 5–80% Radix *Bupleuri* (*Bupleurum chinense*), 1–40% Radix *Astragali* (*Astralagus membranaceus*); and 1–40% *Chrysanthemum Morifolium* (*Chrysanthemum morifolium*).

3. The composition of claim 2, wherein said herbal extracts comprises by weight percent: 10–70% Radix *Gentianae Longdancao* (*Gentianae longdancao*); 10–70% Fructus *Xanthii Sibirici* (*Xanthii sibirici*); 10–70% Radix *Bupleuri* (*Bupleurum chinense*), 1–30% Radix *Astragali* (*Astralagus membranaceus*); and 1–30% *Chrysanthemum Morifolium* (*Chrysanthemum morifolium*).

4. An antiviral pharmaceutical composition comprising effective amounts of extracts of the five herbs: Radix *Gentianae Longdancao* (*Gentianae longdancao*), Fructus *Xanthii Sibirici* (*Xanthii sibirici*), Radix *Bupleuri* (*Bupleurum chinense*), Radix *Astragali* (*Astralagus membranaceus*), and *Chrysanthemum Morifolium* (*Chrysanthemum morifolium*), said composition having a therapeutic index of between at least 80 and 400; and a pharmaceutically acceptable excipient.

5. The pharmaceutical composition of claim 4, wherein said herbal extracts comprise by weight percent: 5–80% Radix *Gentianae Longdancao* (*Gentianae longdancao*); 5–80% Fructus *Xanthii Sibirici* (*Xanthii sibirici*); 5–80% Radix *Bupleuri* (*Bupleurum chinense*), 1–40% Radix *Astragal* (*Astralagus membranaceus*); and 1–40% *Chrysanthemum Morifolium* (*Chrysanthemum morifolium*).

6. The pharmaceutical composition of claim 5, wherein said herbal extracts comprise by weight percent: 10–70% Radix *Gentianae Longdancao* (*Gentianae longdancao*); 10–70% Fructus *Xanthii Sibirici* (*Xanthii sibirici*); 10–70% Radix *Bupleuri* (*Bupleurum chinense*), 1–30% Radix *Astragali* (*Astralagus membranaceus*); and 1–30% *Chrysanthemum Morifolium* (*Chrysanthemum morifolium*).

7. The pharmaceutical composition of claim 4, wherein said composition is administered by a parenteral, intramuscular, subcutaneous, oral, sublingual, intravenous, intravaginal, intraural, intraocular, nasal, bronchial, transdermal or topical route.

8. The composition of claim 1, wherein said herbal extracts are powdered extracts or liquid extracts.

9. The pharmaceutical composition of claim 4, wherein said herbal extracts are powdered extracts or liquid extracts.

* * * * *